June 26, 1956 F. MEILLAND Plant Pat. 1,489
ROSE PLANT
Filed July 8, 1955
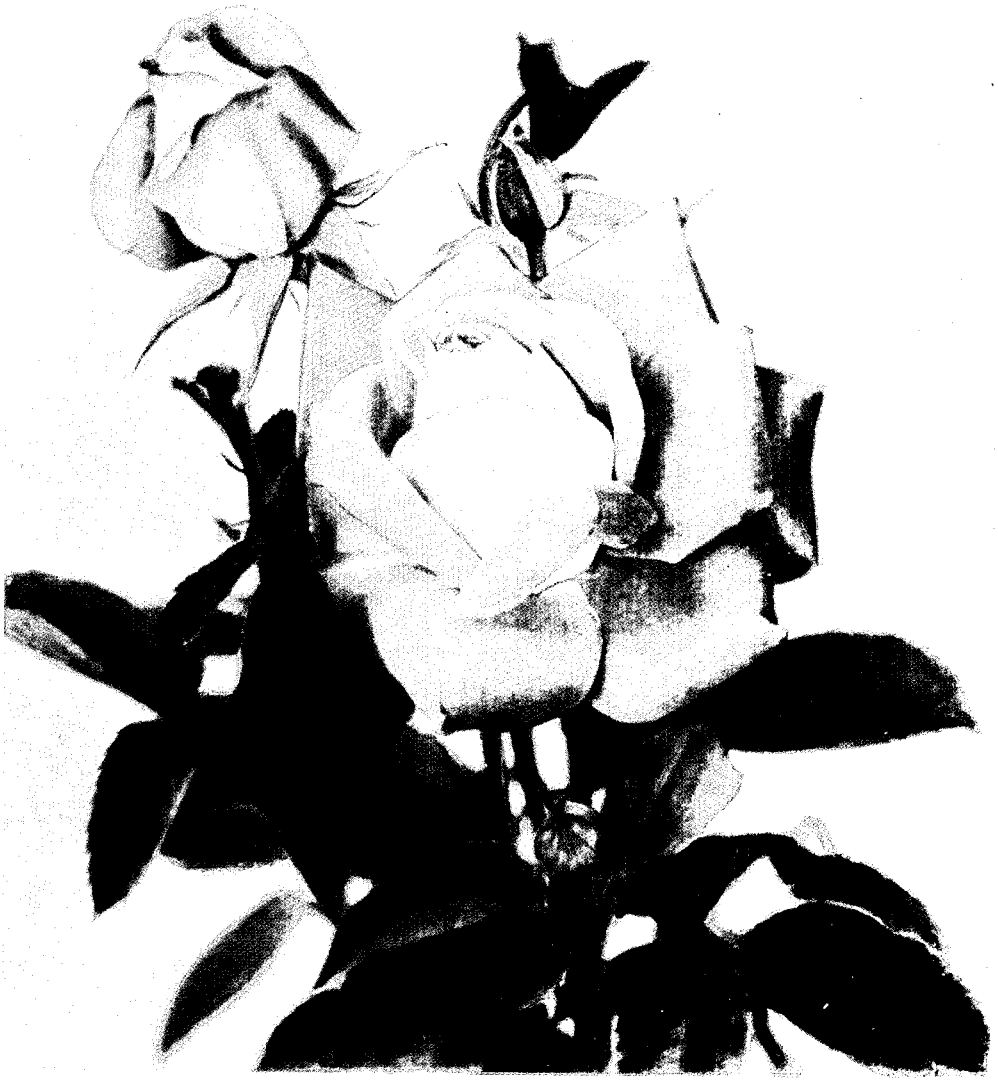
Inventor.
Francis Meilland
By: Robb & Robb
Attorneys.

United States Patent Office

Plant Pat. 1,489

Patented June 26, 1956

1,489

ROSE PLANT

Francis Meilland, Cap Azura, Cap d'Antibes, Alps Maritime, France, assignor to The Conard-Pyle Company, West Grove, Pa., a corporation of Pennsylvania Application July 8, 1955, Serial No. 520,943

Claims priority, application France July 30, 1954

1 Claim. (Cl. 47—61)

The present invention relates to a new and distinct variety of rose plant of the hybrid tea class, which was originated by me by crossing the well-known variety "Peace" (Plant Patent No. 591) with the variety "Independence" (Plant Patent No. 1036), the latter being known in Germany as "Kordes' Sondermeldung."

As the result of this breeding, I have produced a new rose variety which is particularly characterized as to novelty by its vigorous habit of growth, abundant foliage, good resistance to blackspot, large, full blooms of excellent form, and the distinctive two-toned color of its blooms, the petals of said blooms being iridescent Rose Red on their inner surface, and being White, suffused with Pink, on their reverse surface.

The foregoing characteristics definitely differentiate the new variety from its parents, as well as from all other varieties of which I am aware, and asexual reproduction of the new variety by budding, as performed both in France and at West Grove, Pennsylvania, U. S. A., shows that said characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—"Peace."
*Pollen parent.*—"Independence" ("Kordes' Sondermeldung" in Germany).
Propagation: Holds its distinguishing characteristics through succeeding propagations by budding.

FLOWER

Locality where grown and observed: West Grove, Pennsylvania, U. S. A.
Flowers borne: Singly to stem; on stems of medium length and normal strength.
Quantity of bloom: From moderate to free, outdoors.
Continuity: Continuous.
Fragrance: Slight.

Bud:
*Peduncle.*—Medium length; medium caliper; erect; medium rough; with medium number of red hairs. Color—Oxblood Red, Plate 00823/3.
*Before calyx breaks.*—Size—medium. Form—globular; with a conspicuous neck; with foliaceous appendages on the surface of the bud; with medium, much-cut, bristle-like foliaceous parting extending beyond the tip of the bud equal to ¼ or more of its length.
*As calyx breaks.*—Color—Rose Opal, Plate 022/1, overlaid with heavy streaks of Oxblood Red, Plate 00823/1.
*As first petal opens.*—Size—from medium to large. Form—globular. Color: Outside—main body of petal Spirea Red, Plate 025/1, veined with White; margin of petal Spirea Red, Plate 025. Inside—Crimson, Plate 22, with area surrounding point of attachment Sulphur Yellow, Plate 1/2.
*Opening.*—Opens up well.

Bloom:
*Size (when fully open).*—Large; from 4½ inches to 5 inches.
*Petalage.*—Double; from 45 to 60 petals; arranged regularly.
*Form.*—Globular at first, but becoming cupped; petals being at first loosely rolled outward, but becoming flat later at maturity.

Petals: Leathery; with inside velvety and outside satiny.
*Shape.*—Outer—obovate; usually with 1 or 2 notches, but sometimes having no notches. Intermediate—obovate; usually with 1 notch, but occasionally with 2 notches. Inner—obovate; with apex flat.

This description of a newly opened flower was made from a rose grown outdoors in the month of June, at West Grove, Pennsylvania, U. S. A.:

*Color.*—Outer petal: Outside surface—White, suffused with Rose Pink, Plate 427/2, shading to Rose Pink, Plate 427/3; base of petal Mimosa Yellow, Plate 602/2. Inside surface—Rose Red, Plate 724/1, shading to Sulphur Yellow, Plate 1/3 at base of petal, with point of attachment Sulphur Yellow, Plate 1/2. Intermediate petal: Outside surface—China Rose, Plate 024/1 at margin of petal, shading to White, suffused with Rose Pink, Plate 427/2 and dotted with China Rose, Plate 024/1; base of petal Mimosa Yellow, Plate 602/2. Inside surface—Rose Red, Plate 724, with base of petal Sulphur Yellow, Plate 1/2. Inner petal: Outside surface—Rose Bengal, Plate 25/2 at margin of petal, shading to White, suffused with Rose Pink, Plate 427/2 and blotched with Rose Bengal, Plate 25/2; point of attachment Mimosa Yellow, Plate 602/2. Inside surface—Crimson, Plate 22, with base of petal Sulphur Yellow, Plate 1/1.

This description was made from a rose that was open for 3 days outdoors in the month of June, at West Grove, Pennsylvania, U. S. A.:

*Color.*—Outer petal: Outside surface — White, suffused with Rose Bengal, Plate 25/2 at margin of petal, shading to Rose Bengal, Plate 25/3, with base of petal Empire Yellow, Plate 603/3; point of attachment Empire Yellow, Plate 603/2. Inside surface—China Rose, Plate 024, shading to Mimosa Yellow, Plate 602/2 at base of petal; point of attachment Empire Yellow, Plate 603. Inner petal: Outside surface—White, suffused with Rose Bengal, Plate 25/3, shading to Neyron Rose, Plate 623/3; point of attachment Empire Yellow, Plate 603/2. Inside surface—Crimson, Plate 22, shading to Empire Yellow, Plate 603 at point of attachment.
*General color effect.*—Newly opened flower—Rose Red, Plate 724, with White, suffused with Rose Pink, Plate 427/2 on reverse of petals. 3-days open—China Rose, Plate 024, with White, suffused with Rose Bengal, Plate 25/3 on reverse of petals.
*Behavior.*—Persist.

*Flower longevity.*—On bush in garden—3 or 4 days in June. Cut roses grown outdoors and kept at livingroom temperatures—3 days in June.

REPRODUCTIVE ORGANS

Stamens: Medium number; arranged regularly.
Filaments: Medium number; most with anthers; medium length. Color—Sulphur Yellow, Plate 1/2.
Anthers: All open at once; medium size; occasionally an anther fused with a petaloid. Color—Apricot, Plate 609/1.
Pollen: Moderate. Color—Gold.
Pistils: Medium number.
Styles: Uneven; medium length; medium thickness; very loosely bunched.
Stigma: Color—Mimosa Yellow, Plate 602/2.
Ovaries: Some protrude from calyx.
Hips: None.
Sepals: Permanent; moderately long; straight; spear-shaped.
Seeds: None.

PLANT

Foliage:

*Leaves.*—Compound of usually 5, but occasionally 3 or 7, leaflets; normal abundance; medium size; heavy; leathery.

*Leaflets.* — Shape — ovoid, with apex mucronate. Base—round. Margin—simply serrate.

*Color.* — Mature: Upper surface — Parsley Green, Plate 00962/1; under surface — Willow Green, Plate 000862/1. Young: Upper surface — Oxblood Red, Plate 00823/3; under surface — Oxblood Red, Plate 00823/3.

*Rachis (the supporting stem of the compound leaf).*—Medium weight. Upper side — grooved; prickly. Under side—smooth.

*Stipules.*—Medium length; medium width; with moderately long points turning out at an angle of 45°.

*Disease resistance.*—Very resistant to blackspot as determined by comparison with other varieties grown under comparable cultural conditions at West Grove, Pennsylvania, U. S. A.

Growth:

*Habit.*—Bushy; branched.

*Growth.*—Moderate.

*Canes.*—Medium weight.

*Main stems.*—Color—Spinach Green, Plate 0960/3. Thorns—several; medium length; hooked; pointed downward; with medium length, oval base. Prickles—few. Color—Brown. Hairs—none.

*Branches.* — Color — Oxblood Red, Plate 00823. Thorns—several; hooked; pointed downward; with medium length, oval base. Prickles—few. Color—Brown. Hairs—none.

*New shoots.* — Color — Oxblood Red, Plate 00823. Thorns—several; medium length; hooked; pointed downward; with medium length, oval base. Prickles—none. Hairs—none.

I claim:

A new and distinct variety of rose plant of the hybrid tea class, substantially as herein shown and described, characterized particularly as to novelty by its vigorous habit of growth, abundant foliage, and good resistance to blackspot, its large, full blooms of excellent form, and the distinctive two-toned color of its flowers, the petals of which are irridescent Rose Red in general color tonality on their inner surface and White, suffused with Pink in general color tonality on their reverse surface.

No references cited.